United States Patent [19]
Yushina et al.

[11] Patent Number: 4,957,868
[45] Date of Patent: Sep. 18, 1990

[54] CYLINDRICAL HOLLOW CARRIERS FOR MICROORGANISMS MADE OF NONWOVEN FABRIC

[75] Inventors: Yoshinori Yushina; Jun Hasegawa; Hiromi Satoh, all of Yokohama, Japan

[73] Assignee: Chiyoda Chemical Engineering & Constructions Co., Ltd., Yokaham, Japan

[21] Appl. No.: 239,185

[22] Filed: Aug. 31, 1988

Related U.S. Application Data

[63] Continuation-in-part of Ser. No. 805,275, Dec. 5, 1985, abandoned.

[30] Foreign Application Priority Data

Dec. 24, 1984 [JP] Japan .................. 59-270719
Jun. 20, 1988 [JP] Japan .................. 63-150117

[51] Int. Cl.$^5$ .................. C12M 1/40; C12N 11/00; C12N 11/02; C12N 11/08
[52] U.S. Cl. .................. 435/288; 435/174; 435/177; 435/180; 435/813
[58] Field of Search .............. 435/174, 176, 177, 179, 435/180, 182, 288, 813

[56] References Cited

U.S. PATENT DOCUMENTS

| | | | |
|---|---|---|---|
| 3,705,084 | 12/1972 | Reynolds | 435/182 X |
| 3,850,751 | 11/1974 | Messing | 435/176 |
| 4,149,937 | 4/1979 | Messing et al. | 435/176 |
| 4,307,151 | 12/1981 | Yamauchi et al. | 435/180 X |
| 4,326,009 | 4/1982 | Royer | 428/407 |
| 4,610,962 | 9/1986 | Takagi et al. | 435/179 |

FOREIGN PATENT DOCUMENTS 186125 7/1986 European Pat. Off. .
122039 7/1983 Japan .................. 435/180

OTHER PUBLICATIONS

Noguchi et al., Chemical Abstracts 105:151582d, 1986.
Encyclopedia of Polymer Science and Technology, vol. 9 (1968), published by John Wiley and Sons, Inc., pp. 345–355.
Encyclopedia of Plastics Equipment, Edited by H. R. Simonds, published by Reinhold Publishing Corp. (1964), pp. 394–401.
Encyclopedia of Textiles, Fibers and Nonwoven Fabrics, Edited by M. Grayson, published by John Wiley and Sons, Inc. (1984), pp. 252–266.

Primary Examiner—David M. Naff
Attorney, Agent, or Firm—Frishauf, Holtz, Goodman & Woodward

[57] ABSTRACT

A cylindrical hollow carrier for microorganisms is prepared by subjecting a nonwoven fabric having a specific gravity of not greater than 1.0 to a surface smoothing treatment at an elevated temperature of 200° to 450° C., then pressing with a roller to give the nonwoven fabric a thickness of 1 to 5 mm and a weight per unit area of 30 to 300 mg/cm$^2$ and then forming the nonwoven fabrics into a cylindrical hollow shape. The carrier has a compression weight of not less than 400 g, and preferably an outer diameter of about 25 to 100 mm and a length of about 40 to 60 mm. The nonwoven fabric may be formed of 35 to 90% fibers of 50 to 600 denier and 10 to 65% fibers of 20 to 1 denier.

20 Claims, 3 Drawing Sheets

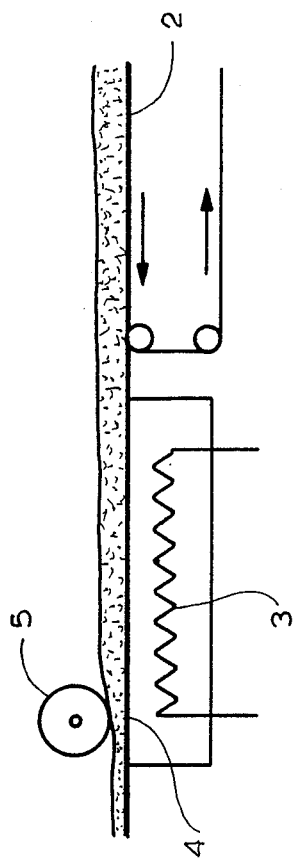
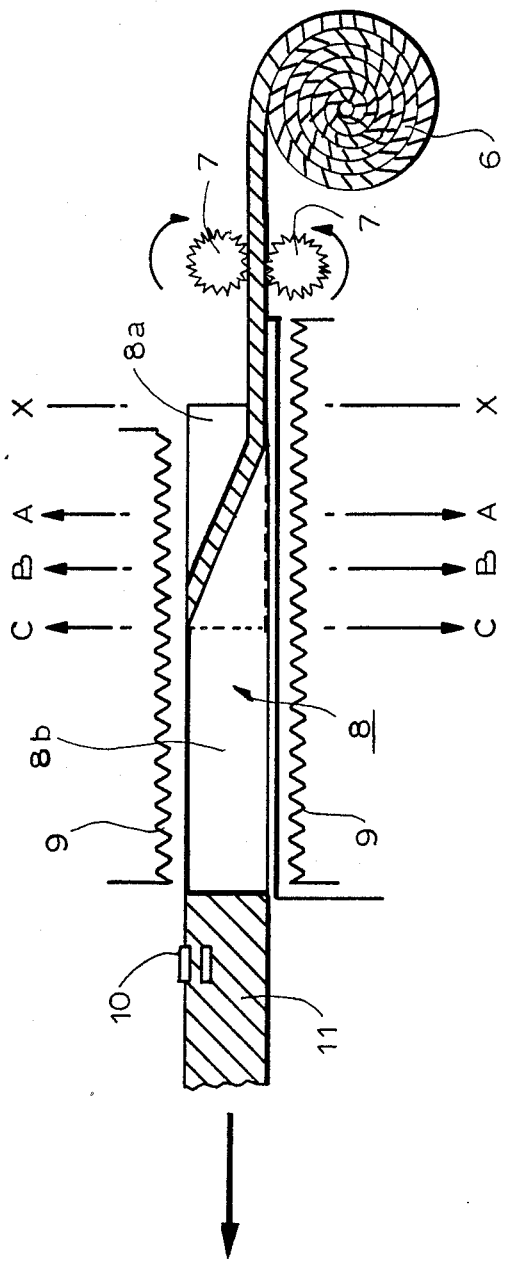

CYLINDRICAL HOLLOW CARRIERS FOR MICROORGANISMS MADE OF NONWOVEN FABRIC

This is a continuation-in-part application of U.S. patent application Ser. No. 06/805,275 which was filed Dec. 5, 1985 now abandoned.

BACKGROUND OF THE INVENTION

The present invention relates to a method for producing a carrier for microorganisms and more particularly, to a method for producing a carrier for microorganisms which is packed in a device for biological reaction (bioreactor) used for treatment of water, production by fermentation or the like and capable of maintaining microorganisms in a high concentration.

In recent years, a technique for continuously performing a reaction by immobilizing microorganisms in a bioreactor has been often adopted. The technique includes, for example, a carrier binding which comprises immobilizing microorganisms onto a water-soluble carrier by an ion binding or covalent binding method, a crosslinking method which comprises strengthening cell walls or cell membranes of microorganisms using a reagent having two or more functional groups and at the same time, effecting crosslinking between the microorganisms, an inclusion method which comprises including microorganisms into a high molecular gel matrix or including them into semipermeable high molecular thin membrane microcapsules, etc.

The present invention is not directed to such methods for immobilizing microorganisms but relates to a method for producing the carrier for microorganisms in a method for adhering and immobilizing microorganisms to a carrier.

In old trickling filters, crushed stone, cokes, etc. are generally used as such an adhesive type carrier for microorganisms; in high speed trickling filters, synthetic resin plates, synthetic resin rings, etc. are used; and in rotary disc devices, synthetic resin plates and other activated charcoal, porous ceramics, naturally occurring inorganic particles, synthetic resin particles, etc. are used. Microorganisms are biologically adhered to these carriers. These carriers of adherence type have been used in bioreactors for treatment of water or production by fermentation in the form of fixed bed type, fluidized bed type or floating bed type. A concentration of microorganisms adhered varied depending upon carrier so that kind of carriers for microorganisms affects efficacy of bioreactors. In general, a specific surface area ($m^2/m^3$) of carrier becomes an important factor; the larger the specific surface area, the larger the concentration of microorganisms adhered.

However, a carrier having a large specific surface area enables to keeping the microorganisms in a high concentration on one hand but on the other hand, silting occurs in a bioreactor due to growth of microorganisms, resulting in various problems such as reduction in efficiency of contacting substrate with microorganisms, reduction in contact efficiency upon supply of a gas containing oxygen, reduction in efficiency of contacting substrate with microorganisms due to an entrapping effect of generated gas, etc.

Accordingly, in order to avoid such problems, a specific surface area value of about 60 to 120 ($m^2/m^3$) is generally adopted, taking as an example a carrier module obtained by laminating synthetic resin plates. A concentration of the microorganisms adhered in this case is merely approximately 2,000 to 3,000 mg/l, when calculated into a volume of exposure tank.

The present applicant has proposed a carrier for microorganisms produced from nonwoven fabrics, etc. which can be used for aerobic or anaerobic bioreactors and can maintain microorganisms in a high concentration 2 or 3 times that in the prior art methods described above (Published Unexamined Japanese Patent Application No. 61-149085).

However, it has become clear that the carrier for microorganisms produced from nonwoven fabrics encounters such a defect that could not be used as a carrier for packing in a commercially available bioreactor in the state shown in Published Unexamined Japanese Patent application No. 61-149085.

Firstly, it has been clarified that the carrier is strongly entangled with each other since it is made of fabrics such as nonwoven fabrics so that fluidization of the carrier becomes difficult. The present applicant has made investigations on coating the surface of the carrier with a film to avoid this problem. However, it has been noted that costs for the coating are extremely large and its commercialization is difficult.

Secondly, it has been noted that carriers produced from nonwoven fabrics or the like are swollen by immersion in water over long periods of time.

Thirdly, it has been noted that carriers produced from nonwoven fabrics or the like have a poor compression strength and distortion of the carriers is unavoidable. Fabrics are originally fragile in strength. In addition, particularly in commercial plant using a large amount of carriers, the carriers are scaled up in the height direction so that a force of compressing onto the carriers increases and the carrier distortion is unavoidable. For this reason, withdrawal of a gas supplied or a gas generated is seriously worsened, resulting in reducing a contact efficiency between microorganisms and substrate. As a result, these methods involve a defect that efficiency of bioreactors becomes low.

The present invention aims at providing a method for producing a carrier for microorganisms capable of eliminating the prior art defects described above, maintaining microorganisms in a high concentration and being sufficiently used for bioreactors of commercial scale.

BRIEF DESCRIPTION

That is, the present invention provides a method for producing a cylindrical hollow carrier for microorganisms having a compression weight of not less than 400 g per carrier which comprises subjecting nonwoven fabrics having a specific gravity of not greater than 1.0 to a surface smoothing treatment at an elevated temperature of 200° to 450° C., then pressing with a roller to give the nonwoven fabrics having a thickness of 1 to 5 mm and a weight per unit area of 30 to 300 mg/cm$^2$ and then forming the nonwoven fabrics into a cylindrical hollow shape.

According to the method of the present invention, nonwoven fabrics are used as materials for the carrier for microorganisms. The nonwoven fabrics are obtained by combining fibrous webs in a laminate layer state and adhering them to each other mechanically or chemically and are used for clothes, medical treatment, heat insulating for building materials and the like. The nonwoven fabrics may be those prepared by any of the direct method and the indirect method, irrespective of preparation method. This art is well established and commercial processes are known which can be used to prepare suitable starting materials. For example, methods for preparing non-woven fabrics useful as starting materials include those methods described in *Encyclopedia of Polymer Science and Technology*, vol. 9 (1968), published by John Wiley and Son, Inc., N.Y., pages 345–355; *The Encyclopedia of Plastics Equipment*, Edited by H. R. Simonds, published by Reinhold Publishing Corp., N.Y. (1964), pages 394–401; and *Encyclopedia of Textiles, Fibers and Nonwoven Fabrics*, Edited by M. Grayson published by John Wiley and Sons, Inc. (1984), pages 252–266. Composite nonwoven fabrics are described in the tables in the Encyclopedia of Textiles, Fibers and Nonwoven Fabrics.

Detailed Description

Figure 3A:
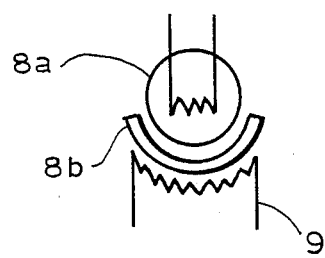
Figure 3B:
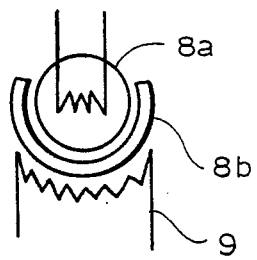

Following known procedures, nonwoven fabrics having a specific gravity of not greater than 1.0 are prepared and used as starting materials for the method of the present invention. As fibrous materials for the nonwoven fabrics, synthetic resins such as polypropylene, polyester, nylon, polyvinyl chloride, polyvinylidene chloride, acryl, polyethylene, vinylon, etc. and preferably having a specific gravity of not greater than 1.0, are preferably used. Composite materials are particularly useful and are obtained by partly incorporating fibrous materials having a specific gravity of not less than 1.0 into polypropylene (specific gravitty of about 0.91), polyethylene (specific gravity of 0.94 to 0.96) or fibrous materials having a specific gravity of not greater than 1.0 thereby to result in a specific gravity of not greater than 1.0.

It is preferred to use fibers having at least two kinds of fineness as the nonwoven fabrics. This results in a carrier for microorganisms having excellent surface smoothness and excellent compression strength. The thick fibers are effective for a compression strength and fine fibers for realizing easy meltability and smoothness in a hot air treatment or surface smoothing treatment later described. As the thick fibers, those having 50 denier or more, preferably 50 to 600 denier are used. On the other hand, those having 20 denier or less, preferably 20 to 1 denier are used as the fine fibers. In the case of using the nonwoven fabrics having thick fibers and fine fibers as such, a mixing rate of both is set to be 35 to 90 wt% of the thick fibers, preferably 40 to 80 wt%, based on the whole fibers. By mixing fibers in such a ratio, it is possible to make the compression weight per one cylindrical hollow carrier for microorganisms finally obtained 400 g or more. Further, depending upon kind of raw nonwoven fabrics, long fibers and short fibers may also be used.

As a shape of the carrier for microorganisms, there are various kinds such as spherical, rectangular parallelepiped or cylindrical shape, etc. According to the method of the present invention, cylindrical hollow carrier for microorganisms is used. This is because the shape is excellent in venting upon gas blowing in a bioreactor.

BRIEF DESCRIPTION OF THE DRAWINGS

FIG. 1 is a schematic representation of the surface smoothing treatment.

FIG. 2 is a schematic representation of a "round shape" forming process.

FIGS. 3(A) and 3(B) show the sections indicated in FIG. 2.

FIG. 4 shows the closing of a fabric cylinder according to the invention.

FIGS. 5(A)–(C) illustrate the compression test described herein.

FIG. 6 illustrates a use of the invention device referring to the Example presented hereinbelow.

Hereafter the method of the present invention will be described by referring to the drawings.

Raw nonwoven fabrics which are very bulky and airy are provided in such a state as having a certain width and length. Steps of preparing the carrier for microorganisms will be described by continuously producing the carrier for microorganisms by carrying the raw nonwoven fabrics on a belt conveyer.

First, prior to the surface smoothing treatment, it is preferred to subject the raw nonwoven fabrics to the following pretreatment.

This pretreatment comprises subjecting the raw nonwoven fabrics to a hot air treatment. Specifically this hot air treatment is carried out, for example, by passing the raw nonwoven fabrics through a hot air chamber as the nonwoven fabrics are put on a belt conveyor. In this case, a temperature of hot air varies depending upon kind of fibrous materials for the nonwoven fabrics used but is generally between 100° and 300° C., preferably between 110° and 250° C. Further a residence time is from 10 seconds to 15 minutes, preferably 30 seconds to 10 minutes. This residence time may be controlled by changing a speed of the belt conveyor. Where the temperature of hot air is overly high or the residence time is excessively prolonged, shrinkage of the raw nonwoven fabrics is seriously excessive and in an extreme case, even thick fibers become fine and melt, which is not preferred. On the other hand, where the temperature of hot air is too low or the residence time is too short, shrinkage of the raw nonwoven fabrics does not occur but the raw nonwoven fabrics remain airy, which is not preferred.

By this hot air treatment, the raw nonwoven fabrics are shrunk. By doing so, fibers, in particular, short fibers melt or shrink, whereby the fibers are hardly split out of the raw fabrics.

Upon the shrinkage, a volume of the raw nonwoven fabrics is reduced to 60 to 80% of that of the original volume.

In the method of the present invention, the raw nonwoven fabrics that are subjected to the pretreatment described above (hot air treatment) if necessary and shrunk are subjected to a surface smoothing treatment. FIG. 1 is an explanatory drawing showing an embodiment of a device used for the surface smoothing treatment.

The raw nonwoven fabrics are carried on a belt conveyer 2 and passed on a metal plate 4 (ordinarily an iron plate) having included therein a heater 3, whereby one surface is subjected to the surface smoothing treatment.

This surface smoothing treatment is substantially actually integrated with a roller compression step subsequent thereto. That is, a roller 5 is provided on the metal plate 4 described above. Subsequently to the surface smoothing treatment with the metal plate 4, compression is effected between this roller 5 and the metal plate 4.

The surfaces of the metal plate 4 and the roller 5 are usually coated with Teflon. Further a heater is also enclosed in the roller 5. Temperatures of the metal plate 4 and the roller 5 are elevated to 200° to 450° C., preferably 300° to 400° C., with the respective heaters enclosed.

In case that the temperature in this case exceeds 450° C., melting of the raw nonwoven fabrics occurs to cause silting the raw nonwoven fabrics and such is not preferred. On the other hand, where the temperature is lower than 200° C., a desired strength is not obtained when the nonwoven fabrics are formed into a cylindrical hollow shape.

The residence time of the raw nonwoven fabrics 1 on the metal plate 4 may vary depending upon fibrous materials for the nonwoven fabrics, heating temperature, etc. and is difficult to primarily determine but is generally 20 to 60 seconds in the case of 200° C.; in the case of 450° C., 2 to 20 seconds. However, for purposes of increasing the preparatory speed, it is practical to set the heating temperature at 350° to 400° C. Where the residence time is prolonged and the temperature is high, the fibers completely melt so that the role of the carrier based on the fibers fails to be exhibited.

Surface melting under the foregoing conditions results n rigid nonwoven fabrics having gas permeability. The surface of the thus obtained nonwoven fabrics at the side of metal plate 4 is free from hairiness but becomes smooth because of the surface smoothing treatment.

The thus obtained nonwoven fabrics are compressed between the roller 5 and the metal plate 4. By controlling a distance between the roller 4 and the metal plate 4, a thickness of the nonwoven fabrics is made 1 to 5 mm, preferably 2 to 4 mm. Where the thickness of the nonwoven fabrics is greater than 5 mm, rounding fabrication is effected only with difficulty because of thick thickness and this is not economical and hence, such is not preferred.

By this roller compression step, the nonwoven fabrics compressed by heat and mechanically can be obtained.

By subjecting to the treatment as described above, a weight per unit area of the nonwoven fabrics is made 30 to 300 mg/cm$^2$, preferably 50 to 200 mg/cm$^2$. When the weight per unit area of the nonwoven fabrics is less than 30 mg/cm$^2$, the nonwoven fabrics are easy to be collapsed. On the other hand, when the weight exceeds 300 mg/cm$^2$, troubles tend to occur in that the rounding fabrication later described is performed only with difficulty and therefore, the weight either exceeding the upper limit or lower than the lower limit is not preferred.

The thus obtained nonwoven fabrics having a thickness of 1 to 5 mm and a weight per unit area of 30 to 300 mg/cm$^2$ are formed into a cylindrical hollow shape as follows.

In order to form the nonwoven fabrics into the cylindrical hollow shape, the nonwoven fabrics are cut with a rotary cutter, etc. having a predetermined width to make shallow nonwoven fabrics. The width may be determined depending upon a diameter of a desired carrier. In the case of forming into a cylindrical hollow shape carrier having an outer diameter of, for example, 50 mm, its width becomes 167 mm based on the following calculation.

$$(50 \text{ mm} \times 3.14) + 10 \text{ mm (width of melt adherence portion)} = 167 \text{ mm}$$

Next, the thus obtained shallow nonwoven fabrics are subject to rounding fabrication to make a cylinder. In this case, the shallow nonwoven fabrics are set so that the surface which has undergone the surface smoothing treatment described above becomes the outer surface of the cylinder. The shallow nonwoven fabrics have a stronger strength than the raw nonwoven fabrics and are thus subjected to rounding fabrication, whereby softness is imparted and the both ends are adhered. The shallow nonwoven fabrics 6 wound into a roll shape are continuously fed into a cylindrical tube 8 for rounding fabrication by feeding gears 7, where rounding fabrication is effected. Here, the circular tube 8 for rounding fabrication is explained. This circular tube 8 for rounding fabrication takes in part a dual tube structure. That is, a portion from the beginning X of the tube to line C—C in FIG. 2 takes a dual tube structure composed of an inner tube 8a and an outer tube 8b. A portion subsequent to line C—C in FIG. 2 is composed of the outer tube 8b alone. In summation, the inner tube 8a is present only between the beginning X of the tube and line C—C in FIG. 2.

The inner tube 8a is a cylindrical tube, which may be hollow or solid. On the other hand, the outer tube 8b takes a shape like a cylindrical hollow tube, the tip of which is cut off obliquely. The circular tube 8 for rounding fabrication is in such a shape that a part of the inner tube 8a is inserted into the tip portion of the outer tube 8b cut off obliquely.

An inner diameter of the outer tube 8b is set to be some or less smaller than the other diameter when the nonwoven fabrics 6 are rounded. For this reason, the nonwoven fabrics 6 subjected to rounding fabrication are overlapped at the both ends thereof and become cylindrical.

This inner tube 8a and the outer tube 8b are heated by heaters 9 and controlled to a temperature of 100° to 250° C., preferably 150° to 200° C.

The shallow nonwoven fabrics 6 are sent through a gap between the inner tube 8a and the outer tube 8b along the outer surface of the inner tube 8a, whereby rounding fabrication is carried out. A residence time of the shallow nonwoven fabrics 6 in the circular tube 8 for rounding fabrication composed of such inner tube 8a and outer tube 8b is 15 seconds to 2 minutes, preferably 20 to 90 seconds. Generally in the case of making a cylinder having a thick thickness, the residence time becomes long. The respective surfaces of the inner tube 8a and the outer tube 8b to which the shallow nonwoven fabrics 6 are in contact are generally coated with Teflon.

By performing rounding fabrication using the device described above, a secondary surface treatment is simultaneously effected.

Figure 4:
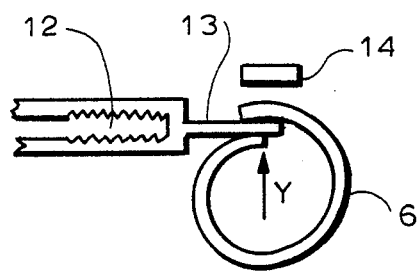

Thus, the shallow nonwoven fabrics 6 are formed into a substantially cylindrical shape by rounding fabrication. Then, the both ends are adhered to each other at heat compression portions 10 to become a nonwoven fabric cylinder 11. FIG. 4 is an explanatory drawing showing a mode of heat compression (adherence) by the heat compression portions 10. The heat compression portions 10 contain a thin metal piece 13 (generally iron piece) heated with a heater 12 which are inserted into the ends of nonwoven fabric cylinder 11. This metal piece 13 is heated to a temperature of 300° to 700° C., preferably 400° to 500° C. Further, a presser foot 14 is provided in the upper portion.

As described above, the inner diameter of outer tube 8b of the circular tube 8 for rounding fabrication is set to be somewhat smaller than the outer diameter when the shallow nonwoven fabrics 6 are rounded.

Therefore, the shallow nonwoven fabrics 6 coming from the circular tube 8 for rounding fabrication are overlapped at the both ends thereof, as shown in FIG. 4.

By adjusting a location of the metal piece 13 to be inserted or a location of the presser foot 14, a width of the overlapping portion in the shallow nonwoven fabrics 6, in other words, a width of the portions to be adhered is set to about 10 mm.

By passing through such heat compression portions 10, adherence is effected. That is, the portion of the shallow nonwoven fabrics 6 which is in contact with the metal piece 13 melts and at a portion Y of the shallow nonwoven fabrics 6, a force is applied to the pressing direction 14 as a force resistant to rounding fabrication so that adherence is effected.

The thus obtained nonwoven fabric cylinder 11 is cut into a uniform length to form carriers.

Here, the cutting is performed primarily by going a heated nichrome wire provided in a uniform space up and down followed by secondary cutting to make carriers having a desired size. In view of a preparation efficiency, it is preferred that the primary cutting be performed during the continuous preparation step. A plurality of nonwoven fabric cylinders having a uniform length obtained by this primary cutting are made a line and the secondary cutting may be performed by a plurality of nichrome wires. The nonwoven fabric cylinder is primarily cut by a 1 m interval. Then, a plurality of the nonwoven fabric cylinders each having a length of 1 m are secondarily cut into 50 mm intervals, whereby 20 carriers per one nonwoven fabric cylinder can be prepared.

A ratio of the outer diameter of the carrier to its length is generally 1:2 to 1:0.5, preferably 1:1. By setting the ratio of the outer diameter to the length in the range described above, the carrier easily moves upon reversed washing in a fluidized bed or a fixed bed, when the carrier is actually packed in a bioreactor.

As described above, the cylindrical hollow shaped carrier for microorganisms having a compression weight of 400 g or more for each carrier can be prepared.

Figure 5A:
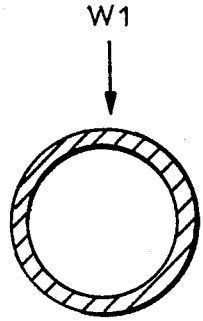
Figure 5B:
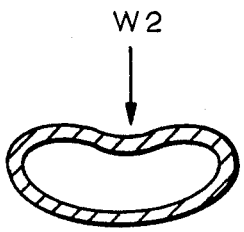
Figure 5C:
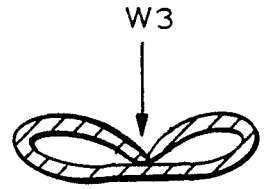

The compression weight for each carrier as used in the present invention refers to a weight $W_3$ when a spot load is applied from the upper part of the cylindrical hollow shaped carrier having an outer diameter of 50 mm × a length of 50 mm, its weight gradually increases ($W_1 \rightarrow W_2 \rightarrow W_3$) and the upper part of the cylindrical hollow shaped carrier is brought into contact with the lower part thereof, as shown in FIG. 5. FIGS. 5(A), (B) and (C) are explanatory drawings showing the method of this compression test.

According to investigations of the present inventors, it has been made clear that the compression weight for each carrier should be 400 g at minimum, desirably 700 g or more, more desirably 1000 g or more in the compression test described above, in view of avoiding distortion of the carrier due to buoyancy when packed in a bioreactor, etc.

According to the method of the present invention as described above, the carrier having a compression weight of 440 to 1560 g for each carrier which sufficiently meets the required value can be prepared.

[Examples]

Next, the present invention will be described in more detail with reference to the examples.

Example 1

Nonwoven fabrics shown in Table 1 were used. First, raw nonwoven fabrics (raw fabrics A) were treated with hot air of 200° C. for 30 seconds.

Then, using a device shown in FIG. 1, the hot air-treated raw nonwoven fabrics 1 were subjected to a surface smoothing treatment under conditions of 400° C. for 15 seconds and at the same time, compressed with a roller. A thickness of the obtained nonwoven fabrics was 2.5 mm and a weight per unit area was 48 mg/m$^2$.

After cutting into a predetermined width, the nonwoven fabrics were formed into a cylindrical hollow shape using a device shown in FIG. 2, which was further cut into a uniform length to give carriers for microorganisms as described in Table 1. A residence time in the circular tube 8 for rounding fabrication of shallow nonwoven fabrics 6 was 20 seconds and, a temperature of inner tube 8a and outer tube 8b was 170° C.

Example 2

Nonwoven fabrics shown in Table 1 were used. First, raw nonwoven fabrics (raw fabrics B) were treated with hot air of 200° C. for a minute.

Then, using a device shown in FIG. 1, the hot air-treated raw nonwoven fabrics 1 were subjected to a surface smoothing treatment under conditions of 400° C. for 20 seconds and at the same time, compressed with a roller. A thickness of the obtained nonwoven fabrics was 3.2 mm and a weight per unit area was 105 mg/m$^2$.

After cutting into a predetermined width, the nonwoven fabrics were formed into a cylindrical hollow shape using a device shown in FIG. 2, which was further cut into a uniform length to give carriers for microorganisms as described in Table 1. A residence time in the circular tube 8 for rounding fabrication of shallow nonwoven fabrics 6 was 30 seconds and, a temperature of inner tube 8a and outer tube 8b was 200° C.

Example 3

Nonwoven fabrics shown in Table 1 were used. First, raw nonwoven fabrics (raw fabrics C) were treated with hot air of 220° C. for 2 minutes.

Then, using a device shown in FIG. 1, the hot air-treated raw nonwoven fabrics 1 were subjected to a surface smoothing treatment under conditions of 400° C. for 40 seconds and at the same time, compressed with a roller. A thickness of the obtained nonwoven fabrics was 4.0 mm and a weight per unit area was 164 mg/m$^2$.

After cutting into a predetermined width, the nonwoven fabrics were formed into a cylindrical hollow shape using a device shown in FIG. 2, which was further cut into a uniform length to give carriers for microorganisms as described in Table 1. A residence time in the circular tube 8 for rounding fabrication of shallow nonwoven fabrics 6 was 40 seconds and, a temperature of inner tube 8a and outer tube 8b was 200° C.

TABLE 1

|  | Example 1 | Example 2 | Example 3 |
|---|---|---|---|
| Nonwoven fabrics | Polypropylene (PP) and polyethylene (PE) | | |
| Fineness of fiber | PP:80, | | PE:7 |

TABLE 1-continued

|  | Example 1 | Example 2 | Example 3 |
|---|---|---|---|
| Mixing rate (wt %) |  | PP/PE = 50/50 |  |
| Temperature in surface smoothing treatment (°C.) |  | 400 |  |
| Time for surface smoothing treatment (second) |  | 15 |  |
| Kind of raw fabrics | A | B | C |
| Thickness after surface smoothing treatment and contact bonding with roller (mm) | 2.5 | 3.2 | 4.0 |
| Weight per unit area after surface smoothing treatment and contact bonding with roller (mg/cm$^2$) | 48 | 105 | 164 |
| Carrier for microorganism: |  |  |  |
| Shape |  | cylindrical |  |
| Size |  | outer diameter or 50 mm × length of 50 mm |  |
| Compression weight (g/carrier) | 440 | 970 | 1560 |
| Surface state | smooth no hairiness | smooth no hairiness | smooth no hairiness |

Application Example

A bioreactor using the carrier obtained by the method of the present invention and a conventional active sludge device were operated in parallel to compare with the conventional method. This comparative continuous run was performed in a bench scale. A device, method and results of the run are as follows.

(1) Device

Figure 6:
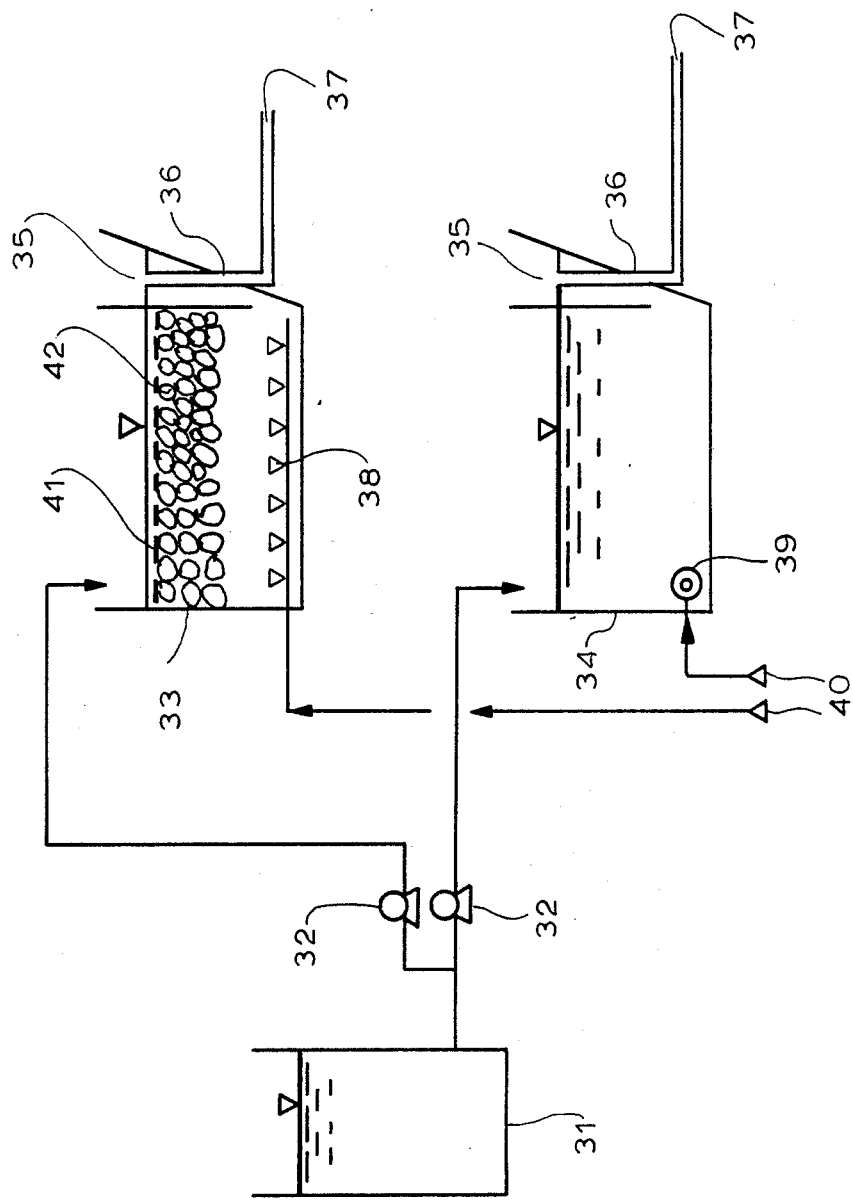

A device shown in FIG. 6 was used for the run. In the figure, numeral 31 is a raw water tank, numeral 32 is a pump for raw water supply, numeral 33 is a bioreactor packed with the carrier, numeral 34 is an active sludge exposure tank, numeral 35 is a precipitation tank, numeral 36 is a treated water line, numeral 37 is treated water, numeral 38 is a venting tube, numeral 39 is an exposure tube, numeral 40 is air and oxygen-containing gas, numeral 41 is a support for the carrier for microorganisms and numeral 42 is the carrier for microorganisms.

Size and volume of the bioreactor 33 packed with the carrier obtained by the method of the present invention and the active sludge exposure tank 34 were both identical and were as follows.

600 mm × 336 mm (width) × 500 mm (effective height) = 100 liters (effective volume)

Further the precipitation tank has a size of 136 mm × 336 mm (width) × 500 mm (effective height) and its effective volume was 11.4 liters.

The bioreactor 33 was packed with 50 liters of the carrier obtained in Example 2 of the present invention. Accordingly, a carrier packing rate in the bioreactor 33 was 50%. The carrier had a floating property so that a lattice-like support 41 for the carrier for microorganisms was provided at the upper portion of bioreactor 3. The support 41 for the carrier for microorganisms is made of transparent vinyl chloride. Each lattice is of square shape having 40 mm each and presses the carrier (outer diameter of 52 mm × length of 52 mm) so as not to float on. A location of the support 41 for the carrier for microorganisms is on a level beneath 50 mm from the water depth.

The exposure tube 39 in the active sludge exposure tank 34 in the active sludge device is provided by only one at the bottom thereof and designed to cause a revolving flow in the tank. The bioreactor packed with the carrier is provided with 7 venting tubes 38 at the bottom thereof, whereby a gas is exposed to the entire carrier packed.

(2) Method

Waste water having a BOD concentration of about 700 mg/l using fish meat extract as substrate was made and used as raw water. The raw water was supplied to the bioreactor 33 packed with the carrier and the active sludge exposure tank 34 from the raw water tank 31 via raw water supply pumps 32, 32. Supply of air was designed to have a dissolved concentration in each tank of about 2 mg/l. A temperature in each tank was controlled to 25° C. and operation was made around neutral pH. A test period was that initial one month was used for acclimation of bacteria and adherence to the carrier and then continuous operation was made for the following 2 months. During the continuous run, a BOD volume load was stepwise changed to 1.0, 2.1 and 3.0 kg BOD/m$^3$.tank.D, whereby change in quality of treated water was examined in each tank.

(3) Results

The results are shown in Table 2. From the results, it has been made clear that in 1.0 kg BOD/m$^3$.tank.D, the quality of treated water was slightly better with the bioreactor packed with the carrier obtained by the method of the present invention but where the BOD load increased, the difference became obviously large and good results were obtained with the bioreactor packed with the carrier obtained by the method of the present invention.

TABLE 2

|  | Invention[*1] | Control[*2] | Invention[*1] | Control[*2] | Invention[*1] | Contol[*2] |
|---|---|---|---|---|---|---|
| Mean BOD of raw water (mg/l) |  | 691 |  | 722 |  | 706 |
| Mean inflow amount (l/hr) |  | 6 |  | 12 |  | 18 |
| Residence time (hr) |  | 16.7 |  | 8.3 |  | 5.6 |
| BOD volume load (kg BOD/m³.tank.D) |  | 1.0 |  | 2.1 |  | 3.0 |
| Mean BOD in treated water (mg/l) | 6 | 14 | 9 | 32 | 18 | 78 |
| BOD removal rate (%) | 99.1 | 98.0 | 98.8 | 95.5 | 97.5 | 89.0 |

[*1] Method using bioreactor packed with the carrier obtained by the method of the present invention
[*2] Active sludge method

[Effects of the Invention]

The carrier for microorganisms obtained by the method of the present invention has a smooth surface and is free from hairiness and entanglement in the bioreactor. In addition, swelling is minimized even in immersion in water and compression strength is high.

Accordingly, the carrier for microorganisms obtained by the method of the present invention can maintain the microorganisms in a high concentration and is sufficiently usable in a bioreactor of commercial scale.

What is claimed is:

1. A method for producing a cylindrical hollow carrier for microorganisms having a compression weight of not less than 400 g per carrier which comprises subjecting a nonwoven fabric having a specific gravity of not greater than 1.0 to a surface smoothing treatment at an elevated temperature of 200° to 450° C., then pressing with a roller to give the nonwoven fabric a thickness of 1 to 5 mm and a weight per unit area of 30 to 300 mg/cm² and then forming the nonwoven fabrics into a cylindrical hollow shape; said compression weight being measured by applying a spot weight to an upper part of the cylindrical hollow shaped carrier having an outer diameter of 50 mm and a length of 50 mm and gradually increasing the weight until the upper part is brought into contact with the lower part.

2. The method of claim 1, wherein the surface smoothing treatment temperature is 300° to 400° C.

3. The method of claim 2, wherein said thickness of the nonwoven fabric is 2 to 4 mm.

4. The method of claim 3, wherein said weight per unit area is 50 to 200 mg/cm².

5. The method of claim 4, wherein said cylindrical hollow shape has an outer diameter of about 25 to 100 mm.

6. The method of claim 5, wherein said cylindrical hollow shape is longer than 100 mm and further comprising cutting said cylindrical hollow shape into cylinders of about 40–60 mm long.

7. The method of claim 1, wherein said thickness of the nonwoven fabric is 2 to 4 mm.

8. The method of claim 1, wherein said weight per unit area is 50 to 200 mg/cm².

9. The method of claim 1, wherein said cylindrical hollow shape has an outer diameter of about 25 to 100 mm.

10. The method of claim 1, wherein said nonwoven fabric is formed of 35 to 90% of fibers of 50 to 600 denier and 10% to 65% of fibers of 20 to 1 denier.

11. A hollow cylindrical carrier for microorganisms having a compression weight of not less than 400 g per carrier, said carrier being made by a process which comprises subjecting a nonwoven fabric having a specific gravity of not greater than 1.0 to a surface smoothing treatment at an elevated temperature of 200° to 450° C., then pressing with a roller to give a nonwoven fabric a thickness of 1 to 5 mm and a weight per unit area of 30 to 300 mg/cm² and then forming the nonwoven fabrics into a cylindrical hollow shape; said compression weight being measured by applying a spot weight to an upper part of the cylindrical hollow shaped carrier having an outer diameter of 50 mm and a length of 50 mm and gradually increasing the weight until the upper part is brought into contact with the lower part.

12. The carrier of claim 11, wherein the surface smoothing treatment temperature is 300° to 400° C.

13. The carrier of claim 12, wherein said thickness of the nonwoven fabric is 2 to 4 mm.

14. The carrier of claim 13, wherein said weight per unit area is 50 to 200 mg/cm².

15. The carrier of claim 14, wherein said cylindrical hollow shape has an outer diameter of about 25 to 100 mm.

16. The carrier of claim 15, wherein said cylindrical hollow shape is longer than 100 mm and further comprising cutting said cylindrical hollow shape into cylinders of about 40–60 mm long.

17. The carrier of claim 16, wherein said thickness of the nonwoven fabric is 2 to 4 mm.

18. The carrier of claim 17, wherein said weight per unit area is 50 to 200 mg/cm².

19. The carrier of claim 18, wherein said cylindrical hollow shape has an outer diameter of about 25 to 100 mm.

20. The carrier of claim 19, wherein said nonwoven fabric is formed of 35 to 90% of fibers of 50 to 600 denier and 10% to 65% of fibers of 20 to 1 denier.

* * * * *